(12) United States Patent
Rittman et al.

(10) Patent No.: US 11,638,523 B2
(45) Date of Patent: May 2, 2023

(54) PUSH-BUTTON AND TOUCH-ACTIVATED VITAL SIGNS MONITORING DEVICES AND METHODS OF MAPPING DISEASE HOT SPOTS AND PROVIDING PROXIMITY ALERTS

(71) Applicants: Danny Rittman, San Diego, CA (US); Mo Jacob, Beverly Hills, CA (US)

(72) Inventors: Danny Rittman, San Diego, CA (US); Mo Jacob, Beverly Hills, CA (US)

( * ) Notice: Subject to any disclaimer, the term of this patent is extended or adjusted under 35 U.S.C. 154(b) by 334 days.

(21) Appl. No.: 16/983,289

(22) Filed: Aug. 3, 2020

(65) Prior Publication Data
US 2021/0298600 A1 Sep. 30, 2021

Related U.S. Application Data

(60) Provisional application No. 63/012,205, filed on Apr. 19, 2020, provisional application No. 63/001,564, filed on Mar. 30, 2020.

(51) Int. Cl.
*A61B 5/00* (2006.01)
*A61B 5/024* (2006.01)
(Continued)

(52) U.S. Cl.
CPC ........ *A61B 5/0008* (2013.01); *A61B 5/02438* (2013.01); *A61B 5/6802* (2013.01); *A61B 5/6832* (2013.01); *G06N 3/02* (2013.01); *G06N 5/01* (2023.01); *H04W 4/021* (2013.01); *H04W 4/023* (2013.01)

(58) Field of Classification Search
CPC . A61B 5/0008; A61B 5/02438; A61B 5/6802; A61B 5/6832; G06N 3/02; G06N 5/003; H04W 4/021; H04W 4/023
See application file for complete search history.

(56) References Cited

U.S. PATENT DOCUMENTS

2008/0171919 A1* 7/2008 Stivoric ................. A61B 5/318
600/301
2015/0269825 A1* 9/2015 Tran ..................... A61B 5/0022
340/539.12
(Continued)

*Primary Examiner* — Orlando Bousono
(74) *Attorney, Agent, or Firm* — Eric L. Lane; Green Patent Law

(57) ABSTRACT

A device and system for measuring vital signs is provided, which includes a housing and an electronic circuit within the housing. The housing has a pressable button on its front side and a sticky surface on its back side for affixing to an object. The electronic circuit measures and recording vital signs data when activated. The electronic circuit may be activated by pressing and holding the button. The vital signs data comprise one or more of: body temperature, heart rate, blood pressure, and blood oxygenation level. The device may include an artificial intelligence unit that stores, records, and analyzes the vital signs data. The artificial intelligence unit builds a worldwide HOT ZONES database and a body temperature map containing information about regions with people reporting elevated body temperature. The device provides proximity alerts to users showing a Safety Circle so users can maintain distance from users with elevated temperatures. The device may be wearable and the housing or enclosure may be in the form of a bracelet, neckless, or ring.

15 Claims, 15 Drawing Sheets

(51) Int. Cl.
    *H04W 4/021*     (2018.01)
    *H04W 4/02*     (2018.01)
    *G06N 3/02*     (2006.01)
    *G06N 5/01*     (2023.01)

(56) References Cited

U.S. PATENT DOCUMENTS

2017/0296054 A1* 10/2017 Goldstein ............ A61B 5/0008
2020/0113452 A1*  4/2020 Martinez ................ A61B 5/742
2022/0160298 A1*  5/2022 Panneer Selvam .. A61B 5/7455

* cited by examiner

System Operation Logic

Heart Rate And BP Method

System's Mobile app, Communicates With the Device via BT Radio

PUSH-BUTTON AND TOUCH-ACTIVATED VITAL SIGNS MONITORING DEVICES AND METHODS OF MAPPING DISEASE HOT SPOTS AND PROVIDING PROXIMITY ALERTS

CROSS-REFERENCE TO RELATED APPLICATIONS

This application is a non-provisional of and claims priority to U.S. Patent Application No. 63/012,205, filed Apr. 19, 2020, and U.S. Patent Application No. 63/001,564, filed Mar. 30, 2020, each of which is hereby incorporated by reference in its entirety.

FIELD

The present disclosure relates to devices, systems, and methods for measuring and monitoring vital signs, including devices in the shape of a round or pill-shaped button that can be affixed to the back of a mobile phone and activated by pressing and holding a pressable button.

BACKGROUND

As pandemics become more frequent and more serious, maintaining public health will require more efficient ways to remotely monitor the health of individuals. Currently, many vital signs sensing and monitoring devices require medical professionals to operate. Either individuals need to go to medical facilities for vital signs monitoring or medical professionals need to go to where large numbers of people pass through such as airports.

There are many existing home thermometers for temperature sensing and monitoring, but they are not convenient for people to take with them when they leave their homes. Also, they typically do not monitor blood pressure, pulse, or other vital signs. Although there are mobile applications and some wearable devices that sense and monitor vital signs, they may be too complicated for many people to locate, too expensive to afford, and/or too complicated to use.

In a pandemic, it is critical for public health officials and helpful for individuals to know which areas are hot spots for the disease. With that knowledge, healthy people could avoid those areas to slow the spread of the disease Current vital signs monitoring devices are not capable of providing information to a user about other people with elevated temperature or areas with large concentrations of high-temperature people.

Therefore, there exists a need for a vital-signs measuring device that a lay person can use from anywhere without assistance from a medical professional. There also is a need for a vital-signs sensing and monitoring device that measures other vital signs in addition to temperature. There exists a need for a sophisticated vital-signs measuring device that is reasonably priced, easy to use, and convenient to carry. Finally, there is a need for a vital-signs monitoring device and system configured to provide the user with information about hot spot regions with large concentrations of high-temperature people.

SUMMARY

The present disclosure, in its many embodiments, alleviates to a great extent the disadvantages of known vital signs measuring and monitoring devices and systems by providing a device that is in the form of a bracelet or affixed to the back of a mobile phone. Disclosed devices may be in the shape of a round button and be activated by touching or pressing and holding a pressable button. Disclosed systems may utilize artificial intelligence and geolocational data to define regions that may be disease hot spots because they have large concentrations of people reporting above normal body temperatures.

In exemplary embodiments, a device for measuring vital signs comprises a housing and an electronic circuit within the housing. The housing has a pressable button on its front side and a sticky surface on its back side for affixing to an object. The housing may be in the shape of a round or pill-shaped button, and a button battery may be located within the housing. The electronic circuit measures and records vital signs data when it is activated and, in exemplary embodiments, is activated by pressing and holding the button. The vital signs data comprises one or more of: body temperature, heart rate, blood pressure, and blood oxygenation level. The electronic circuit may work in conjunction with a mobile application for a mobile device.

In exemplary embodiments, the device further comprises an artificial intelligence engine. A temperature-sensing microchip may be provided within the housing for body temperature measurement. In exemplary embodiments, the device further comprises an optical electrical system for heart rate, blood pressure, and blood oxygenation measurement. The device may further comprise wireless capability to communicate the vital signs data to an external device. In exemplary embodiments, the device further comprises a geolocation system.

Exemplary embodiments of a device for measuring vital signs comprise an enclosure, an electronic circuit within the enclosure, and an artificial intelligence unit within the enclosure. The electronic circuit measures and records vital signs data when it is activated. The artificial intelligence unit stores, records, and analyzes the vital signs data. The vital signs data comprises one or more of: body temperature, heart rate, blood pressure, and blood oxygenation level. In exemplary embodiments, the enclosure is a bracelet, a neckless, or a ring. In exemplary embodiments, the enclosure is in the shape of a round button having a pressable button on its front side and the device is activated by pressing or touching and holding the button.

In exemplary embodiments, the artificial intelligence unit comprises neural network-based circuitry, at least one deep learning module, a search tree-based decision-making system, and control logic. The deep learning module is configured to conduct location analysis, and the search tree-based decision-making system is configured to conduct proximity analysis and provide alerts. In exemplary embodiments, the alerts are provided when there are abnormalities in one or more of the vital signs data. The control logic is configured to monitor and update the vital signs data and a user's location.

In exemplary embodiments, the artificial intelligence unit builds a worldwide HOT ZONES map database containing information about regions and locations with people reporting elevated body temperature. The device may provide proximity alerts to users showing a Safety Circle so users can maintain distance from users with elevated temperatures. In exemplary embodiments, the device comprises operating software that builds a user's body temperature map, worldwide, such that the user can view the user's body temperature map via a mobile app. The device works with a mobile app and a web-based application, the mobile app and the web-based application being synchronized such that a user may view the body temperature via the mobile app and the web-based application. In exemplary embodiments, the device is configured to be linked with clinics, hospitals, and national health institutions to use the vital signs data to provide real-time proximity alerts. The device may be configured to be connected via a network with all other devices for measuring vital signs associated with other users, thereby creating a private, AI-controlled network to analyze global data and build a worldwide thermal map database.

Exemplary embodiments further comprise a memory chip configured to store prior vital signs data. A battery may be provided and located in the enclosure or located within a separate mobile device in communication with the vital signs measuring device. Exemplary embodiments further comprise a power management system keeping the device in sleep mode until activated to preserve battery life.

In exemplary embodiments, a system for measuring vital signs is embedded in certain commonly used devices. Such systems comprise an electronic circuit measuring and recording vital signs data when activated and an artificial intelligence unit storing, recording, and analyzing the vital signs data. The vital signs data comprise one or more of: body temperature, heart rate, blood pressure, and blood oxygenation level. The system is embedded within a device comprised of a vehicle ignition button, a mobile phone display, a laptop display, a watch display, a tablet display, or an LCD monitor. The system may further comprise a heat sensor embedded within the device display, thereby making the device display heat sensitive.

Accordingly, it is seen that vital signs monitoring and storing devices, systems, and methods are provided which may be affixed to the back of a mobile phone, activated by touching or pressing and holding a pressable button, and may utilize artificial intelligence and geolocational data to define regions that may be disease hot spots. These and other features of the disclosed embodiments will be appreciated from review of the following detailed description, along with the accompanying figures in which like reference numbers refer to like parts throughout.

BRIEF DESCRIPTION OF THE DRAWINGS

The foregoing and other objects of the disclosure will be apparent upon consideration of the following detailed description, taken in conjunction with the accompanying drawings, in which.

DETAILED DESCRIPTION

Figure 1A:
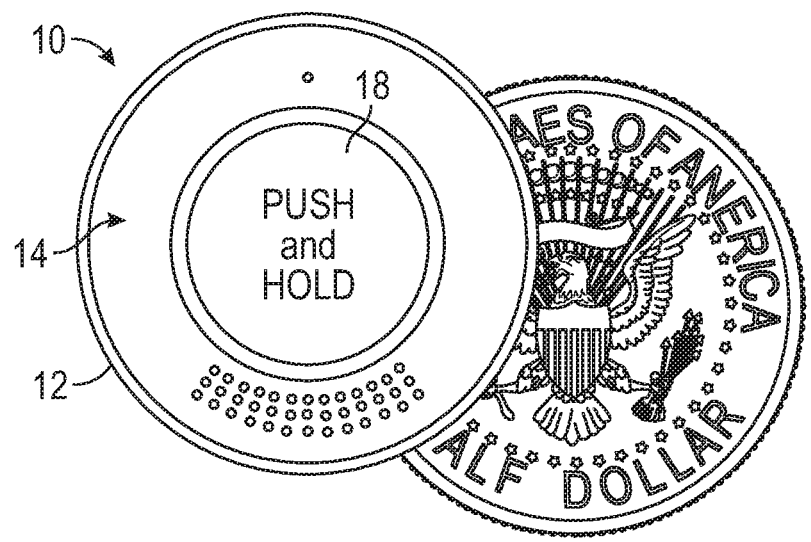
FIG. 1A is a front view of an exemplary embodiment of a device for measuring vital signs in accordance with the present disclosure.

In the following paragraphs, embodiments will be described in detail by way of example with reference to the accompanying drawings, which are not drawn to scale, and the illustrated components are not necessarily drawn proportionately to one another. Throughout this description, the embodiments and examples shown should be considered as exemplars, rather than as limitations of the present disclosure.

As used herein, the "present disclosure" refers to any one of the embodiments described herein, and any equivalents. Furthermore, reference to various aspects of the disclosure throughout this document does not mean that all claimed embodiments or methods must include the referenced aspects. Reference to materials, configurations, directions, and other parameters should be considered as representative and illustrative of the capabilities of exemplary embodiments, and embodiments can operate with a wide variety of such parameters. It should be noted that the figures do not show every piece of equipment, nor the materials, configurations, and directions of the various circuits and communications systems.

With reference to FIGS. 1A-4, exemplary embodiments of a device for measuring vital signs will be described. Device 10 has a housing 12 with a front side 14 and a back side 16. Electronic circuitry comprising at least one electronic circuit 20 is located in the housing 12 and may be within flexible PCB within the housing. As discussed in more detail herein, the electronic circuit 20, when activated, measures and records the vital signs data of the user. In exemplary embodiments, housing 12 includes a pressable button 18 on its front side 14. The user activates the electronic circuit 20 to measure vital signs data by pressing and holding the pressable button 18. The normal or default condition of the device 10 is OFF, and the device turns ON only when a user pushes the ON/MEASURE button 18. In exemplary embodiments, the ON/MEASURE button 18 needs to be pressed for several seconds, e.g., 5-10, to turn the device 10 ON to measure the user's vital signs as described in more detail herein. The user's vital signs may be measured during that brief time in which the button 18 is pressed down. Once the button 18 is released, the device 10 is switched back to the default OFF state to conserve power.

The pressable button 18 may be located on part of the front side 14 of the housing 12 such as in the center of the front side. Alternatively, the entire front side 14 could consist of the pressable button 18 such that pressing the front side 14 of the housing 12 means pressing the button 18. As best seen in FIG. 1, housing 12 may be round and, more particularly, the housing may be in the shape of a round button. The housing may be in the shape of a pill-shaped button. A button shaped device may come equipped with a replaceable power source such as a button battery, e.g., CR 3032. The button may have a biometric option to quickly identify the user according to his/her fingerprint. This feature is provided to ensure users' privacy. The button also may be activated by touch, i.e., a touch button.

Figure 1B:
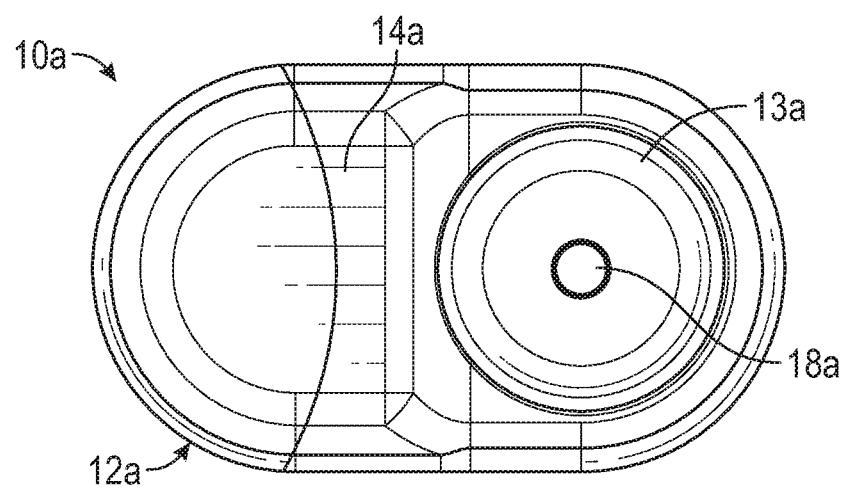
FIG. 1B is a front view of an exemplary embodiment of a device for measuring vital signs in accordance with the present disclosure.
Figure 1C:
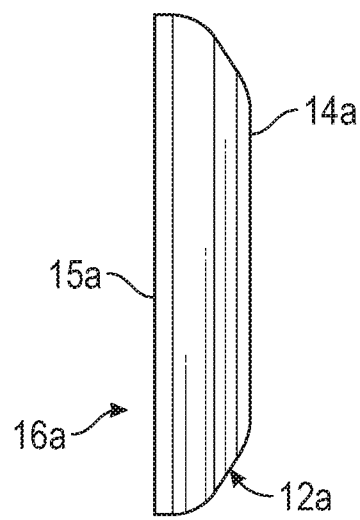
FIG. 1C is a bottom view of the device for measuring vital signs of FIG. 1B.
Figure 1D:
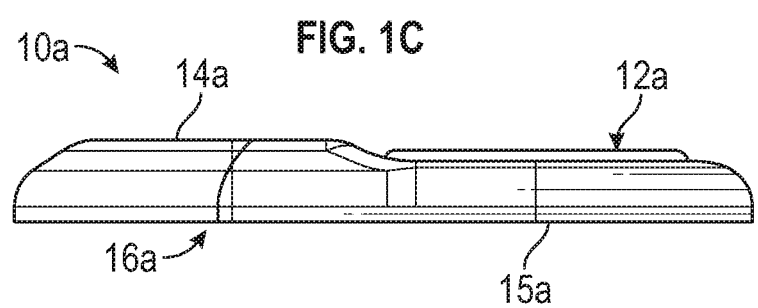
FIG. 1D is a side view of the device for measuring vital signs of FIG. 1B.

As shown in FIGS. 1B, 1C and 1D, device 10a may have a substantially oval-shaped housing 12a. One half of the front side 14a of the device 10a may have a circular portion 13a with the ON/MEASURE button 18a in the center of the circular portion. In exemplary embodiments, the device 10, 10a may be affixed to another object. Advantageously, the device 10, 10a may be affixed to the back side of a mobile phone or other mobile device so it is convenient for the user to carry the device with him or her when on the go. The device could be provided having a sticky surface 15a on the back side 16, 16a of the housing 12, 12a. The entire back side 16, 16a of the housing 12, 12a could be sticky and/or a peel-away adhesive or other type of adhesive 15a could be provided on the device 10, 10a.

Figure 2:
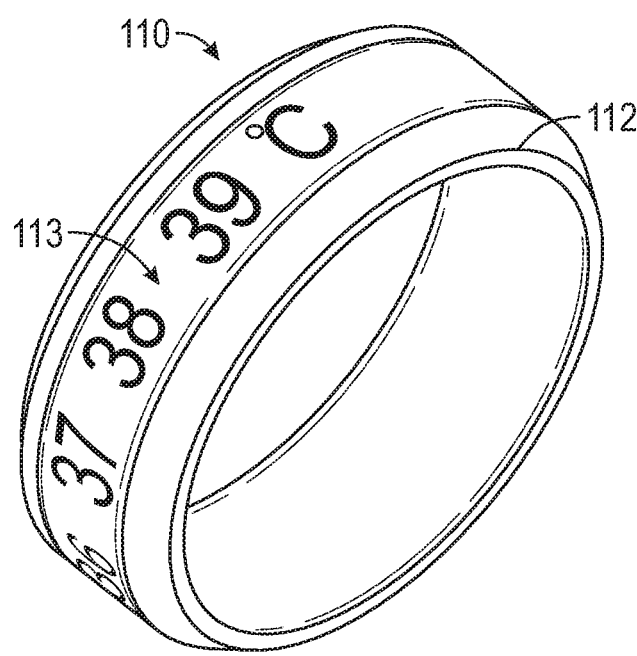
FIG. 2 is a perspective view of an exemplary embodiment of a device for measuring vital signs in accordance with the present disclosure.
Figure 3:
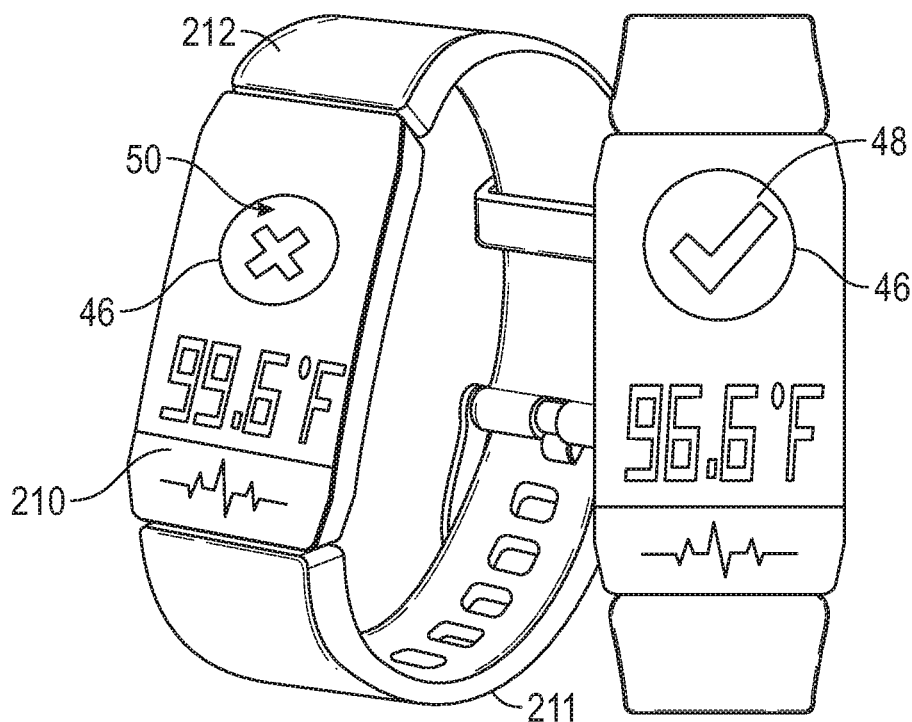
FIG. 3 is a perspective view of an exemplary embodiment of a device for measuring vital signs in accordance with the present disclosure.

Alternatively, the device for measuring vital signs can be in other wearable forms so it is convenient for the user to carry the device with him or her. As shown in FIGS. 2 and 3, the housing or enclosure 112 could be in the form of a bracelet 110. In exemplary embodiments, the bracelet 110 presents the user's vital signs in numerical digits 113 and changes colors according to the body temperature of the user. If the user's temperature is above normal, the numerical digits may turn red and flash to signal the temperature abnormality. Alternative bracelets 212, as illustrated in FIG. 3, may come with wristbands 211 so they can be put on the user's wrist like a watch. In such embodiments, the device 210 is attached to the wristband 211. Devices could come in other convenient wearable variations where the enclosure is in the form of a ring or the device is integrated into other jewelry such as a necklace. In each case, all the electronic circuitry, system components, hardware and software discussed herein would be located in the device enclosure no matter its shape or form.

Figure 6:
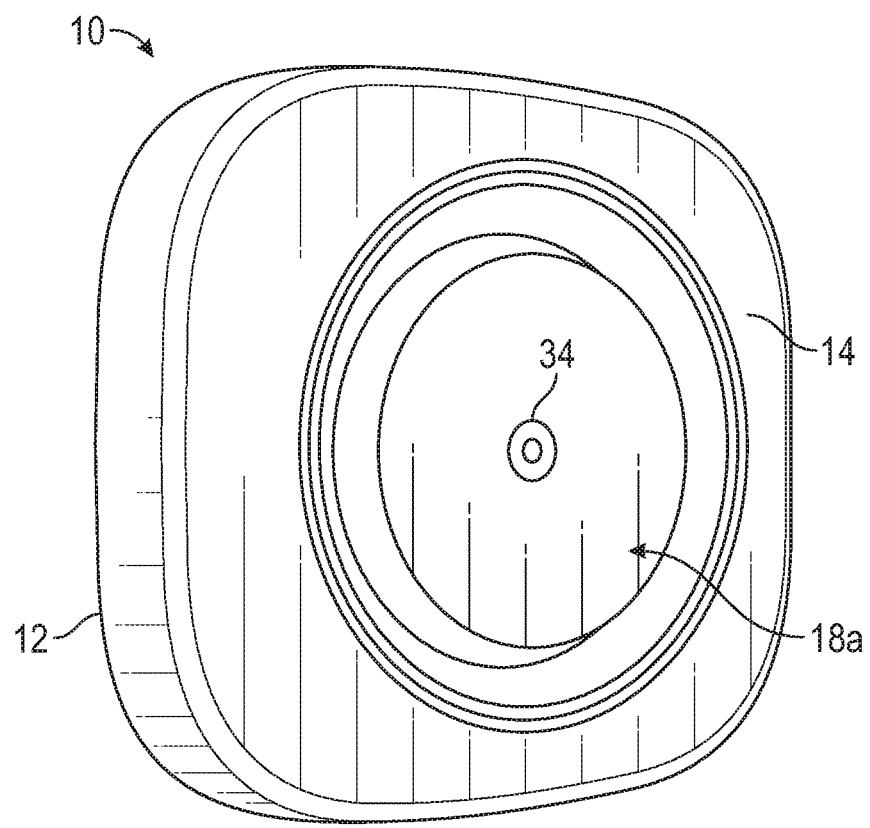
FIG. 6 is a perspective view of an exemplary embodiment of a device for measuring vital signs in accordance with the present disclosure.

Turning to FIGS. 5-8C, exemplary embodiments of a device and system of measuring and storing vital signs contain certain electronic circuitry, hardware and software, and sensing components as described in more detail herein. Generally, an exemplary device has an optical-based, human vital signs (BP, Heart rate) detection and measurement system as well as a body temperature measurement system. A transmission system 30 is provided to send the information to a mobile app via Bluetooth technology. A power management system 32 also may be provided. As best seen in FIG. 6, a hybrid button 18a may include heat and optical sensing systems 34. As discussed in more detail herein, the system may have an associated mobile app for setups and alerting in case of abnormal vitals.

Exemplary on-board computer circuitry in the device includes one or more CPUs or micro-controllers 36, one more memory units 38, and an arithmetic logic unit (ALU). An interface circuit may be provided to enable wireless operation with mobile devices. Control logic 40 provides visual display operation. As discussed in more detail herein, an artificial intelligence (AI) unit may be provided to analyze and record the vital signs data on a remote server via a system network and provide HOT ZONES maps. A memory chip could be utilized to store prior vital signs data for any embodiments, including for a stand-alone device.

Figure 7A:
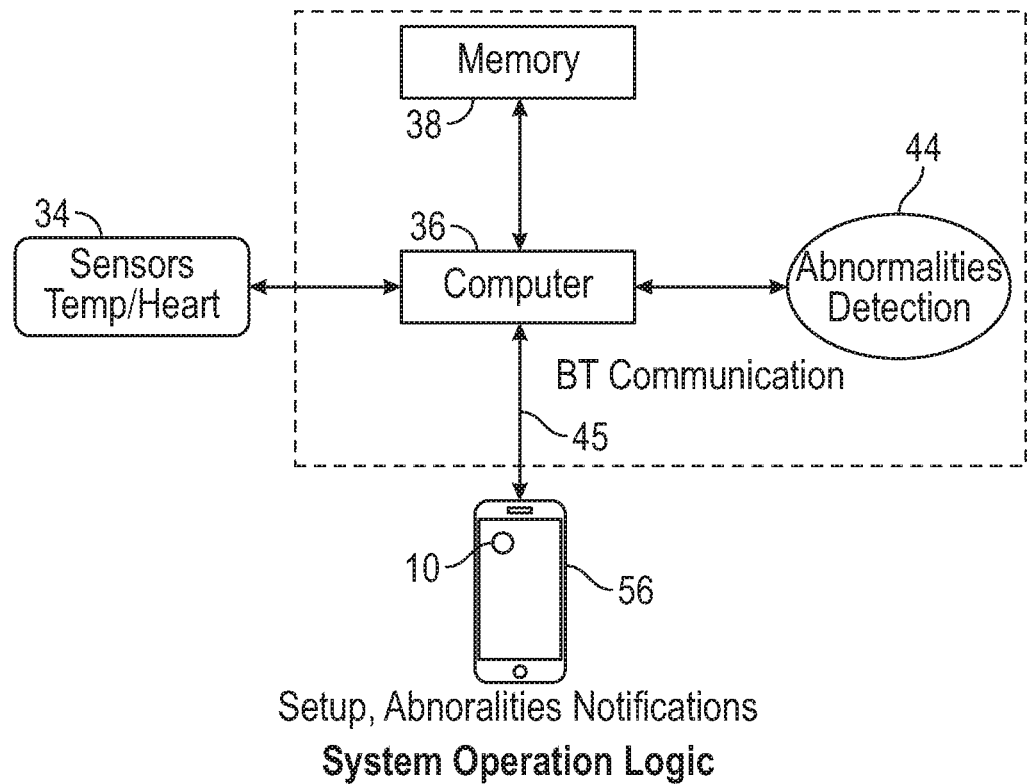
FIG. 7A is a schematic of an exemplary embodiment of a device and system for measuring vital signs in accordance with the present disclosure.
Figure 7B:
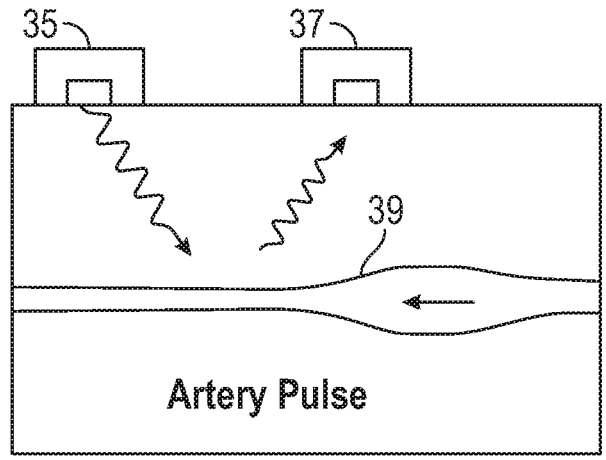
FIG. 7B is a schematic of an exemplary embodiment of heart rate and blood pressure measurement methodology employed by a device and system for measuring vital signs in accordance with the present disclosure.
Figure 8A:
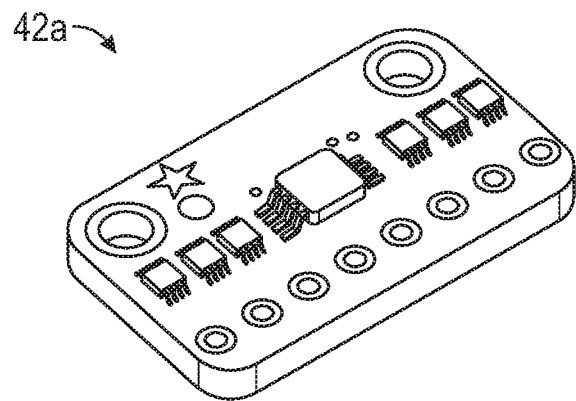
FIG. 8A is an exemplary embodiment of a thermal sensor microchip in accordance with the present disclosure.
Figure 8B:
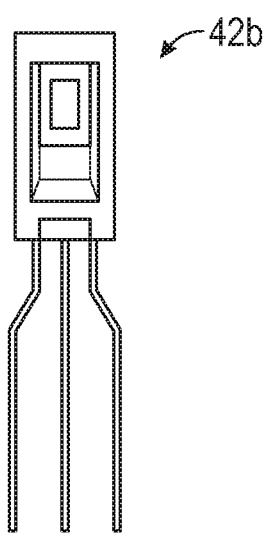
FIG. 8B is an exemplary embodiment of a thermal sensor microchip in accordance with the present disclosure.
Figure 8C:
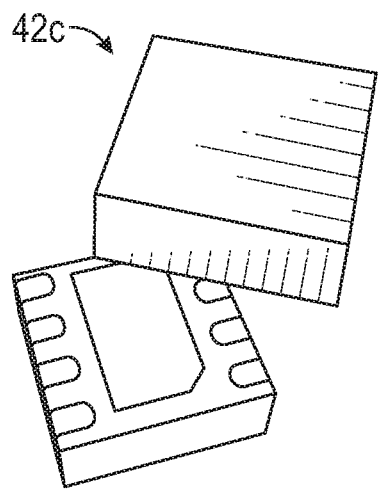
FIG. 8C is an exemplary embodiment of a thermal sensor microchip in accordance with the present disclosure.

Exemplary embodiments of the device 10, 10a, 110, 210, 310 measure vital signs, including but not limited to, body temperature, heart rate, blood oxygenation level, and blood pressure (systolic and diastolic). The device includes a vitals sensing system 34 (temperature, blood pressure, pulse) and an analysis computerized circuitry. As shown in FIG. 7B, heart rate and blood pressure may be measured by a combination of a transmitter 35 and receiver 37 that detect these vital signs data through the user's skin. The transmitter 35 and receiver 37 can use any suitable technologies, including but not limited to, electromagnetic signals and telemetry, for transmitting and detecting this data from a user's artery 39 or from the heart. In exemplary embodiments, electronic circuitry with a temperature sensing microchip 42 measures body temperature. Exemplary thermal sensor microchips 42a, 42b and 43c are shown in FIGS. 8A, 8B and 8C. However, any temperature sensing technology could be used.

Thermocouple, Resistive Temperature Device (RTD), Thermistor, and the newest technology, the Integrated Silicon Based Sensors, could all be utilized in disclosed embodiments. There are other sensing technologies, such as Infrared (Pyrometers) and Thermal Pile, which could also be used. Each of these sensor technologies caters to specific temperature ranges and environmental conditions. The sensor's temperature range, ruggedness, and sensitivity are just a few characteristics that could be considered by a person skilled in the art to determine whether the device would satisfy the requirements of the application. No single temperature sensor is right for all applications. The thermocouple's wide temperature range is unrivalled, as is the excellent linearity of the RTD and the accuracy of the Thermistor. For body temperature, exemplary embodiments use integrated silicon or thermistor sensors due to their high accuracy. In button-shaped embodiments, the button includes a thermometer sensor and an optical sensing system 34 to measure heart rate and blood pressure, and the system performs measurement via touch sensor or infra-red based sensor.

In exemplary embodiments, the device 10, 10a, 110, 210, 310 provides abnormalities detection 44 in the form of alerts 46 to the user in the event of vitals abnormalities like high temperature (fever) and heart rate/blood pressure. An LED-based system could be utilized to provide visual feedback to the user about a vital sign parameter such as body temperature. For example, as illustrated in FIG. 3, a green LED 48 lighting up could indicate a normal temperature reading, a yellow LED lighting up (not shown) could indicate a slightly elevated temperature or mild fever, and a red LED 50 lighting up could indicate a high temperature or high fever. The device may maintain, track, and analyze the medical vitals history for each user. Further, exemplary devices and systems can run cross references of a user's medical data, alerting the user about any abnormality that requires medical attention.

Figure 9:
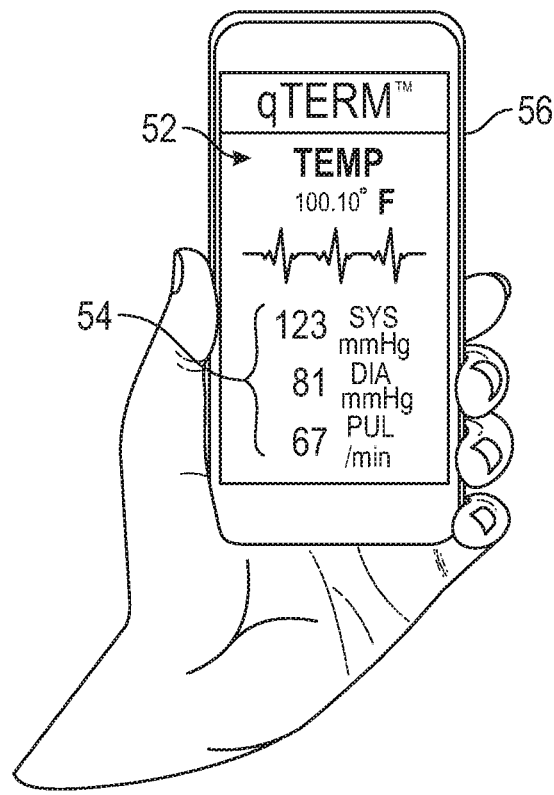
FIG. 9 is front view of an exemplary embodiment of a mobile application in accordance with the present disclosure.
Figure 10:
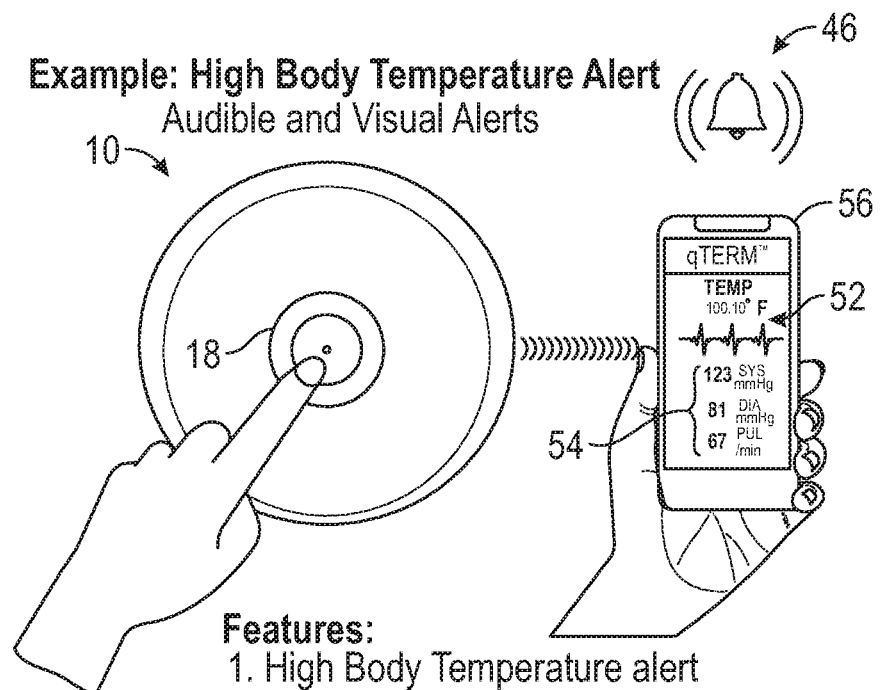
FIG. 10 is a schematic of an exemplary embodiment of a device and system for measuring vital signs in accordance with the present disclosure.

With reference to FIGS. 9 and 10, users will be able to interface and setup the system via mobile software app 52 and/or a web-based application. The user can download an operation mobile application 52 to use with exemplary embodiments of devices for measuring vital signs. The device 10, 10a, 110, 210 may be connected via Bluetooth and/or Wi-Fi wireless 45 and/or short and long radio waves circuitry or any other wireless system to transmit the data to mobile devices or computer or USB or any external device that can store data. When the user pushes the ON/MEASURE button 18, the vital signs data 54 is measured by the device 10, 10a. 110, 210, analyzed by the onboard computerized circuitry to calculate and determine the human vital signs information, and transmitted to the mobile phone 56 or other personal computing device via Bluetooth to present it on the mobile app. The data may be stored on a remote server anonymously. The system detects and alerts the user about her vitals abnormalities via the mobile app. As best seen in FIG. 10, the alerts 46 may be audible and/or visual.

Figure 4:
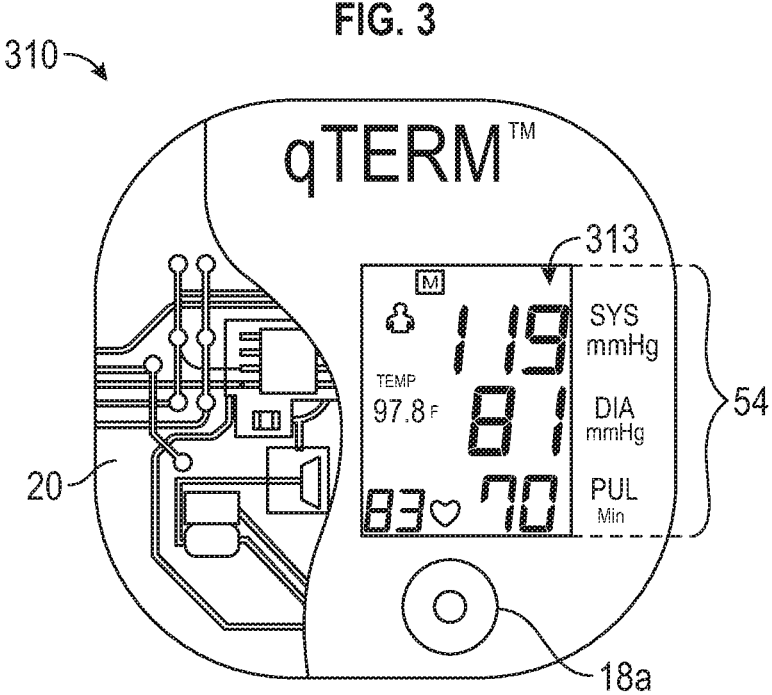
FIG. 4 is a front view of an exemplary embodiment of a device for measuring vital signs in accordance with the present disclosure.
Figure 5:
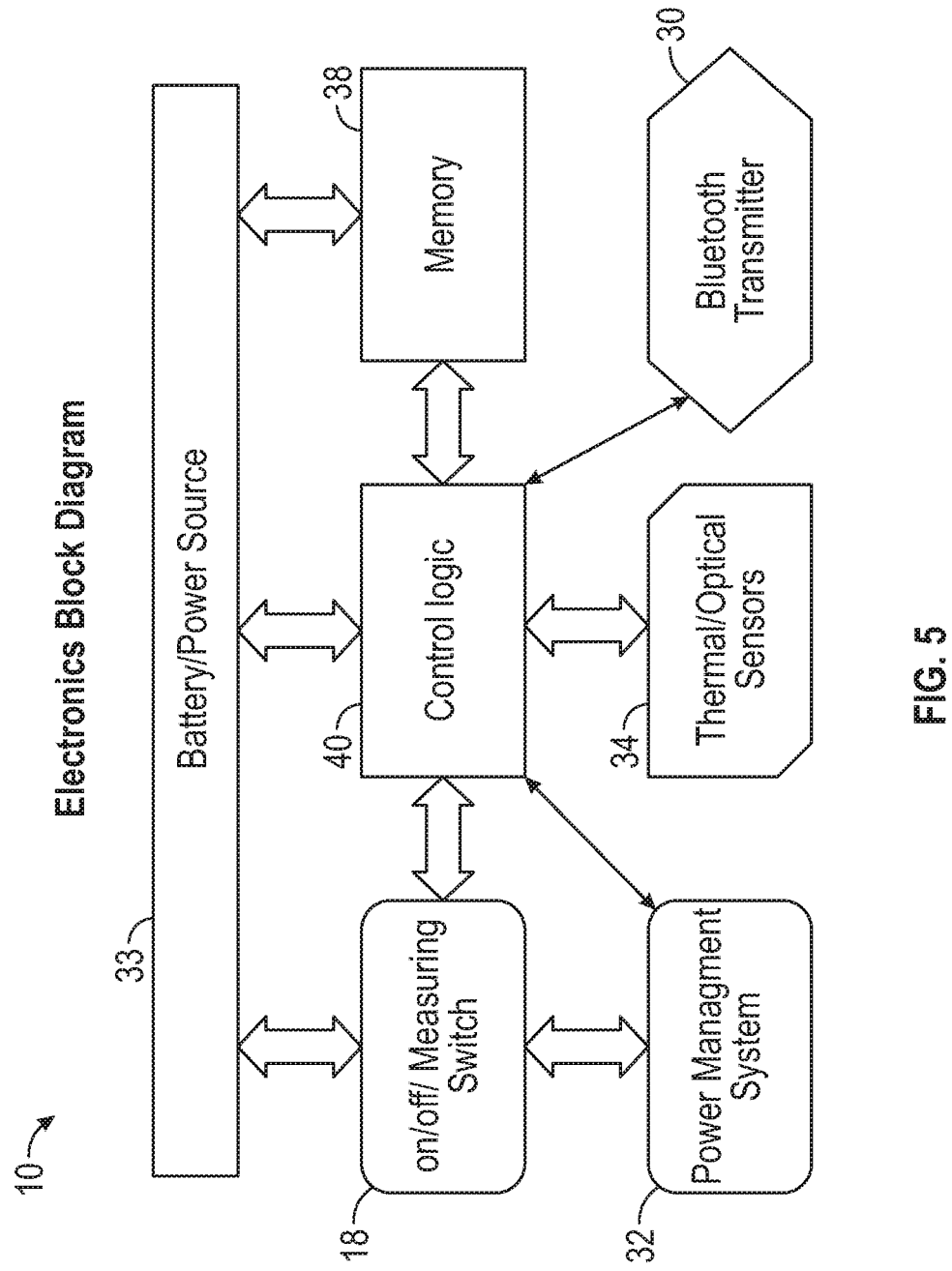
FIG. 5 is a schematic of exemplary internal electronic circuitry, hardware, software, and sensing components of a device for measuring vital signs in accordance with the present disclosure.

Alternatively, the device could be made as a standalone device, without a mobile app and Bluetooth radio. As shown in FIG. 4, an exemplary standalone device 310 includes an ON/measurement button 18a and a touchscreen or LCD display 313, which the user touches to activate and presents the vitals including alerts in case of abnormalities, and built-in software. An independent battery or other power system could be provided with the standalone device.

In exemplary embodiments, the device has an independent power management system 32 and a power source 33 that is activated when a user presses and holds the measuring button 18. The independent power source 33 could be, e.g., a CR 3032 battery. When the button 18 is released the power switches to OFF to preserve battery life. The battery can be charged wirelessly from an external charger or the mobile device battery. The power management system allows for efficient power conservation.

Figure 11A:
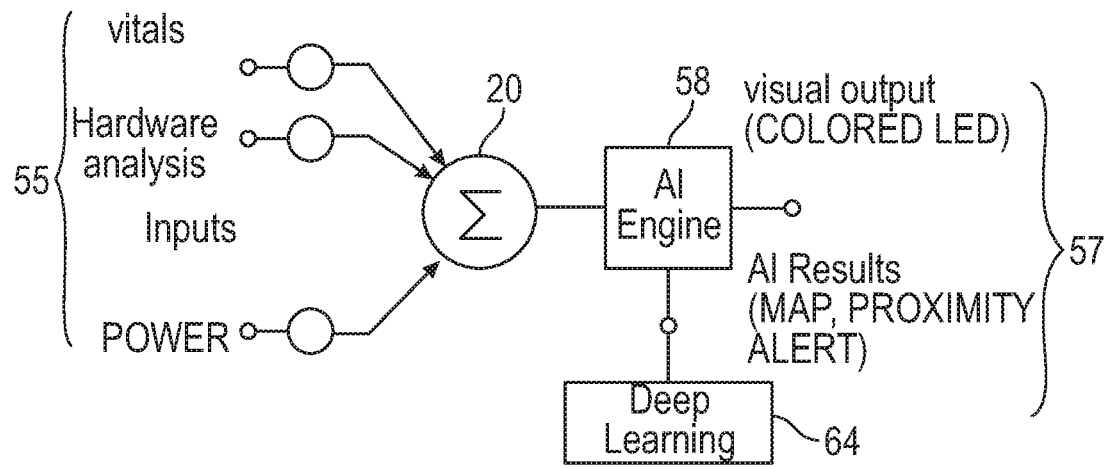
FIG. 11A is a flow diagram showing exemplary general flow of a device and system for measuring vital signs in accordance with the present disclosure.

Turning to FIGS. 11A-13, exemplary embodiments of vital signs measuring systems that provide mapping and proximity alerts by artificial intelligence (AI) will now be described. These disclosed systems can be used with and/or incorporated into the push-button vital signs monitoring device or the bracelet, ring, or any other form of device. FIG. 11A illustrates exemplary general flow of the system. The inputs 55 to the device include the user's vital signs, hardware analysis, and power. These are input into the electronic circuitry 20 and AI unit 58. The outputs 57 include visual outputs such as colors to indicate vital sign abnormalities as well as maps and proximity alerts.

Figure 11B:
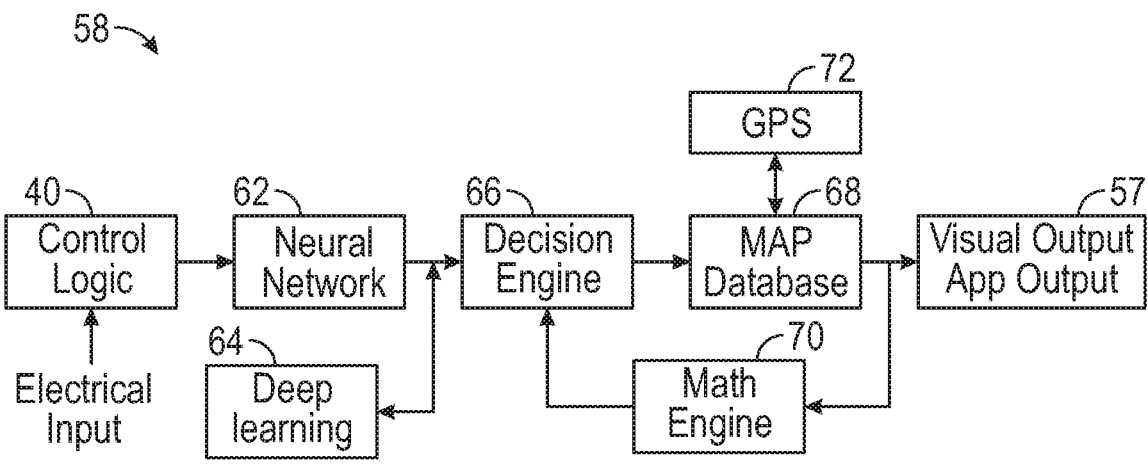
FIG. 11B is a flow diagram showing exemplary general flow including artificial intelligence flow of a device and system for measuring vital signs in accordance with the present disclosure.
Figure 13:
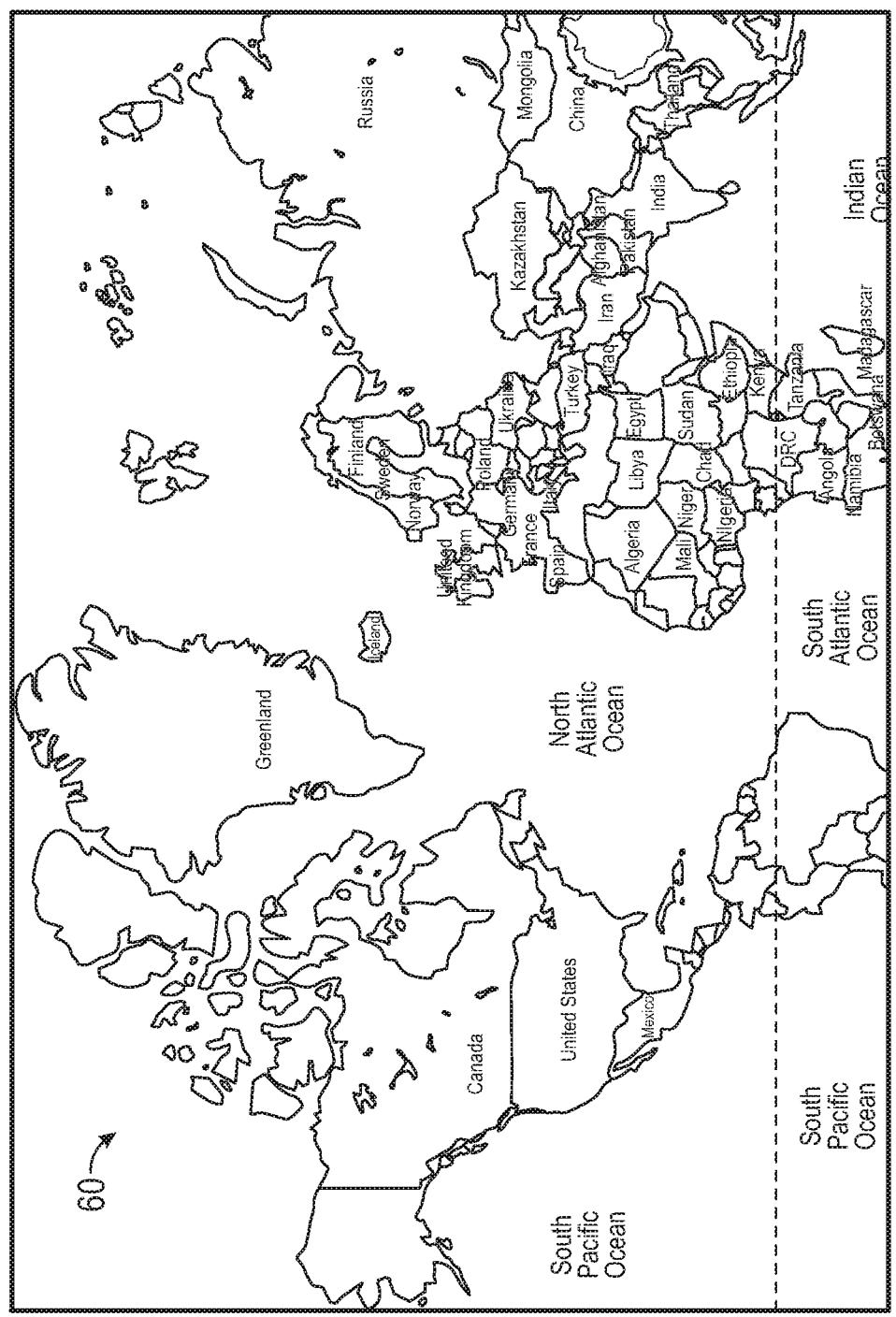
FIG. 13 is an exemplary embodiment of a body temperature map in accordance with the present disclosure.

An exemplary device employs a location system. More particularly, as shown in FIG. 11B, it could use GPS circuitry driving a GPS system 72 to enable location data of the user. The system also could use its own geolocation system or an associated mobile device location system. As discussed above, the device measures and stores data on a user's vital signs, including body temperature. As best seen in FIG. 13, the system's operating software can use that information to build a body temperature map 60 of all users, worldwide, so the users are aware of areas that have a high concentration of people with elevated body temperature and may therefore be disease hotspots. The systems work with a mobile app and a web-based application, with both being synchronized so users can view the body temperature map 60 through their mobile app or online on any device. As discussed in more detail herein, the mobile application synchronized with the web application enables a worldwide HOT ZONES, HOT PERSONS map that includes an alerting system to avoid global virus infection.

In exemplary embodiments, the system and device can provide proximity alerts to users. These proximity alerts, showing a "Safety Circle" within which the user can stay to maintain distance from users with elevated temperatures, are governed by AI. The device's circuitry and accompanying software include an AI system or unit 58 that is based on deep machine learning 64. Exemplary process flow of the AI system 58 is illustrated in FIG. 11B. The built-in AI system has the capability to connect to a central information system and record a population thermal map, based on the user's agreement to share his/her information. The inputs are processed by control logic 40 and a neural network circuitry 62 coupled to a deep machine learning 64 module. A decision engine 66 informed by a math engine 70 communicates the machine learning results to the map database 68. Based on those, the AI system outputs visual and map information, as discussed in more detail herein.

Figure 12:
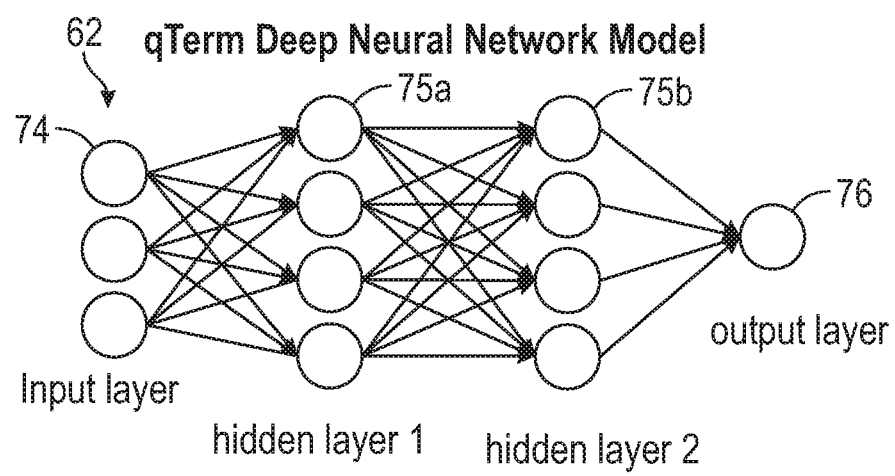
FIG. 12 is a schematic of an exemplary embodiment of a neural network module in accordance with the present disclosure.

More details of exemplary neural network circuitry 62 are shown in FIG. 12, where the input layer 74 communicates with a first hidden layer 75a, which communicates with a second hidden layer 75b, and then to output layer 76. The system can be linked with clinics, hospitals, and national health institutions, e.g., the CDC, to use users' body temperature information to provide real time proximity alerts. The system can update, in real time, the population thermal map according to users' locations. The system is constantly using users' dates, located on a central server and alerting in real time about approaching potentially ill individual(s).

The AI engine enables a "Safety Circle" per users, alerting them about hot spots, worldwide. A HOT SPOT would be a concentration of users with higher than normal body temperature or other abnormal vital signs. More particularly, exemplary embodiments record a user's body temperature, worldwide, and build a HOT ZONES database. The device and system use the mobile device or its own GPS system to categorize and define regions with people that are reporting, e.g., above normal elevated body temperature. The device may be connected via a network with all other devices for measuring vital signs associated with other users, thereby creating a private, AI-controlled network to analyze global data and build a worldwide thermal map database.

A deep learning network secures, controls, and updates the world's thermal map database 68 in real time to provide global, thermal, HOT ZONES alerts. The device and system define a "Safety Circle" to alert the user via audible and visual alerts about getting close to a region with high temperature people. Exemplary embodiments allow the user to define his or her "Safety Circle" perimeter as well. The user can define a proximity safe zone via the mobile app or work with the system defaults. The "Safety Circle" is a proximity alert to notify and alert users in case they are getting closer to a "HOT ZONE", meaning people with high body temperature, i.e., potentially ill individuals. Advantageously, the proximity alerts enable users to avoid HOT ZONES, which contain many potentially ill people and should be avoided to combat viruses.

In exemplary embodiments, the system's machine learning circuitries and software are constantly reviewing the user's body temperature data, recording measurement history, and building worldwide a HOT ZONES thermal map database. An interactive AI engine monitors according to geographical regions 24/7 to alert users in case they are approaching a "hot zone" that indicates possible ill population. The device may label this a health-proximity alert (HPA). Exemplary systems and devices are connected to central health centers of CDC, hospitals and clinics that publish population illness statistics and are targeted to warn users audibly and visually about their proximity to possible sick populations. The device and system collect a user's body temperature information only with their permission, to ensure privacy.

Figure 14:
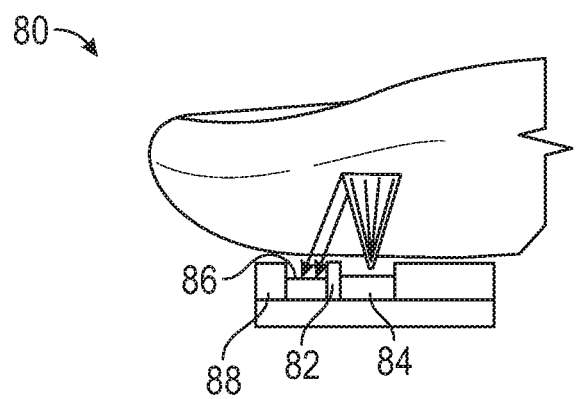
FIG. 14 is a side view of an exemplary embodiment of a device and system for measuring vital signs employing a photoplethysmography method.

Referring to FIG. 14, the device may obtain the vital signs data such as blood pressure and heart pulse by utilizing an optical system that measures volumetric change with LEDs and photodiode from a finger. An exemplary method is photoplethysmography 80, illustrated in FIG. 14, which optically measures the volumetric changes of an organ. The method uses lights and thermal sensors 82 to make measurements. The method measures changes in volume, that is, how big or small something is. The "organ" is not only the heart but the whole cardiovascular system, especially the veins and capillaries under the skin. In simpler terms, optical heart rate tracking is performed using LEDs and a photodiode to measure the changes in the size of blood vessels under the skin. In exemplary embodiments an LED 84 shines a constant light onto the skin. Some of the light 86 is reflected and scattered back into the photodiode 88 that detects these reflections. The heart beats and sends a pressure pulse through the user's circulatory system, and the amount of light that reaches the photodiode changes due to the pressure pulse. An electronic system (on board minicomputer) tracks the changes and the time between pulses and calculates your heart rate and blood pressure.

Figure 15:
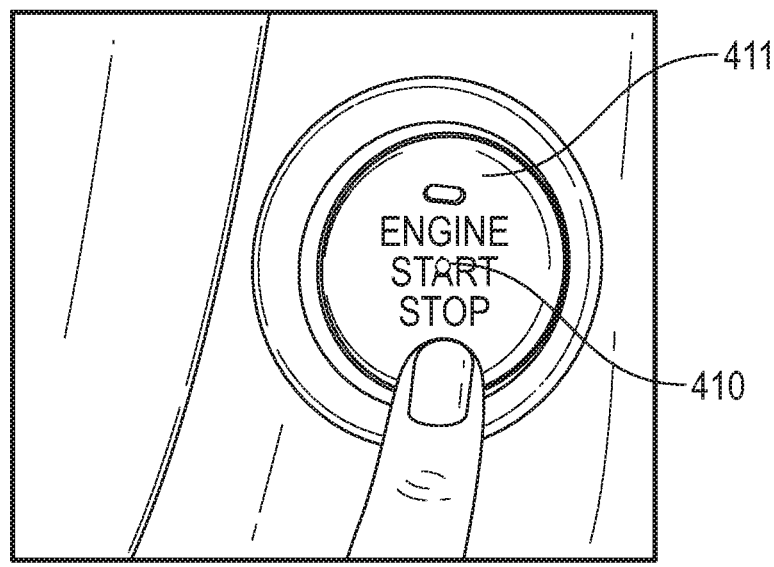
FIG. 15 is a perspective view of an exemplary embodiment of an embedded system for measuring vital signs in accordance with the present disclosure.

Turning now to FIGS. 15, 16A-C, and 17, in exemplary embodiments, a system 410 for measuring vital signs is embedded in certain commonly used devices for added user convenience. In such systems, all the electronic circuitry and features described in detail herein, including tools for measuring and recording vital signs data, artificial intelligence unit, and mapping and proximity alert functions, are embedded in these other devices. For instance, as shown in FIG. 15, the system 410 could be embedded within a vehicle ignition button 411. The system 410 for measuring vital signs could be embedded in or integrated within the digital touchscreen display or monitor of any device, including but not limited to cell phones, tablets, PDMs, laptops, LCD monitors, watches, and a heat sensor may also be embedded within the device display 413 to make it heat sensitive.

Figure 16A:
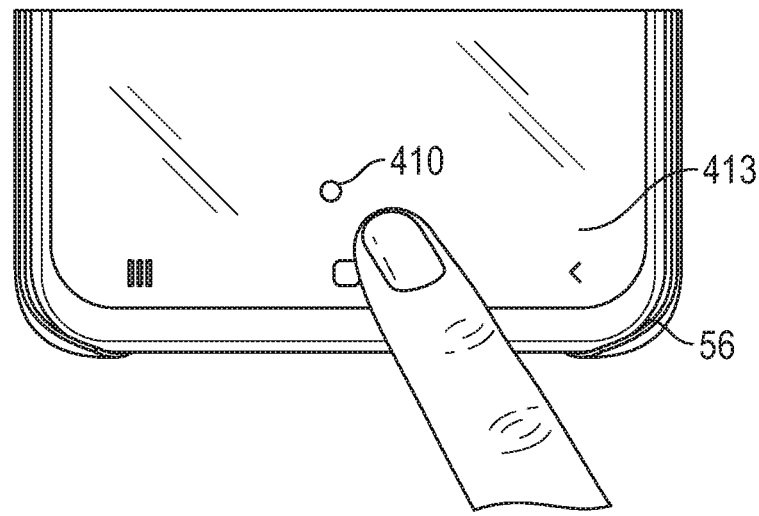
FIG. 16A is a front view of an exemplary embodiment of an embedded system for measuring vital signs in accordance with the present disclosure.
Figure 16B:
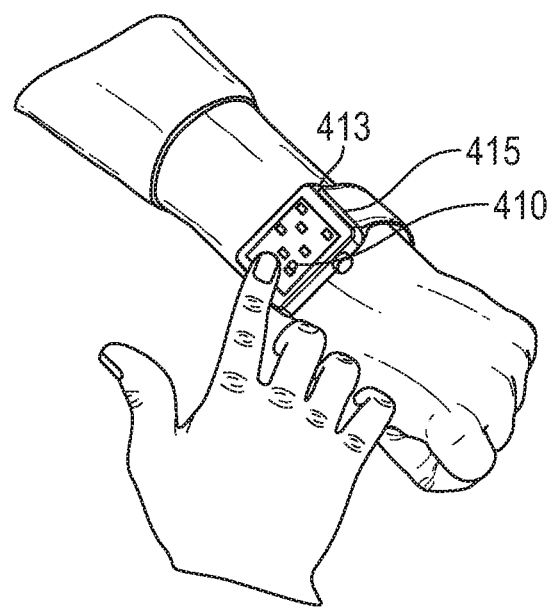
FIG. 16B is a perspective view of an exemplary embodiment of an embedded system for measuring vital signs in accordance with the present disclosure.
Figure 16C:
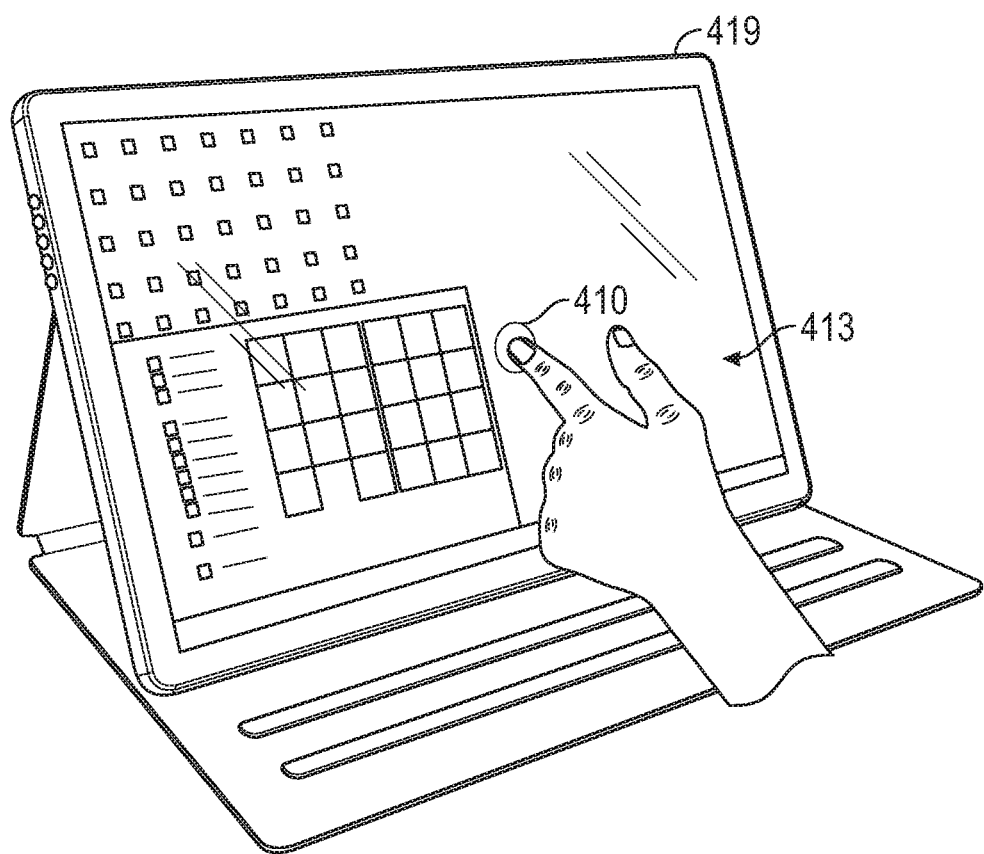
FIG. 16C is a perspective view of an exemplary embodiment of an embedded system for measuring vital signs in accordance with the present disclosure.
Figure 17:
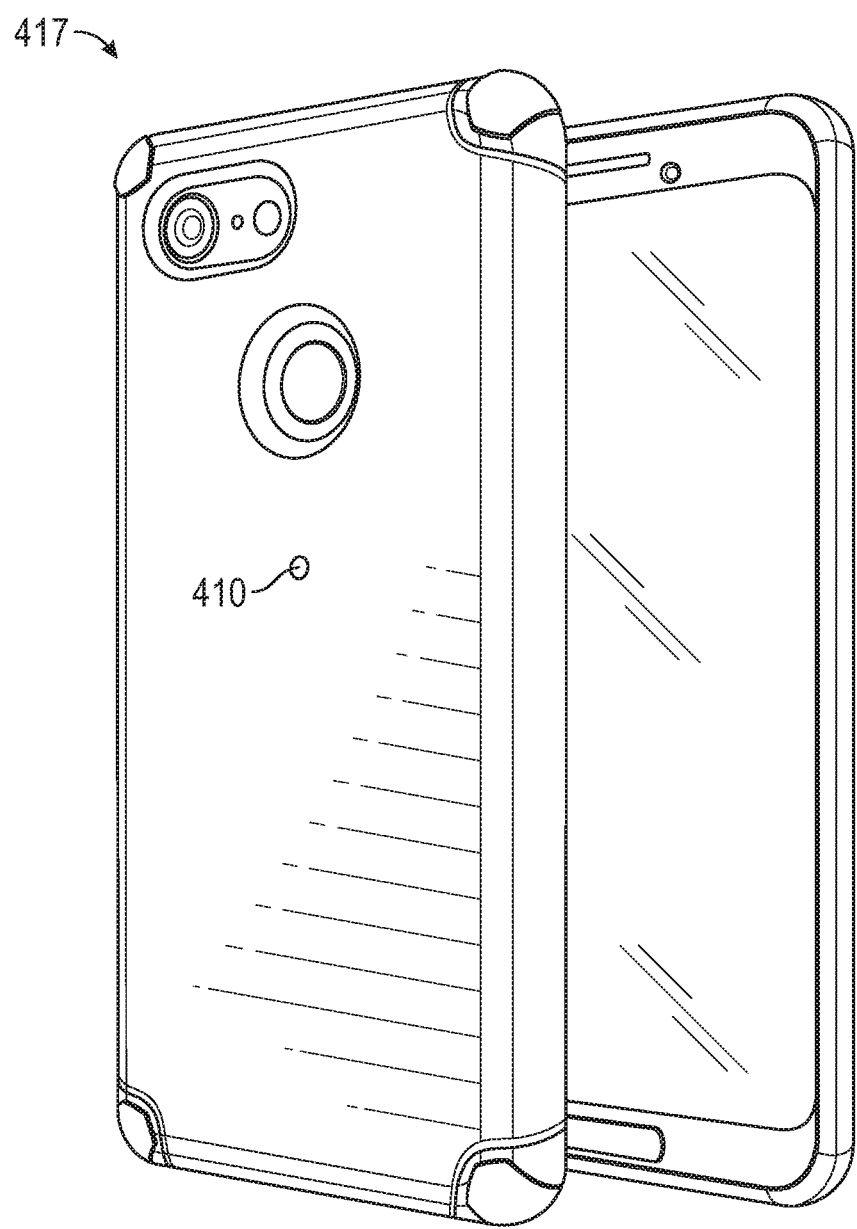
FIG. 17 is a perspective view of an exemplary embodiment of an embedded system for measuring vital signs in accordance with the present disclosure.

For instance, FIG. 16A shows the system 410 embedded in the display 413 of a mobile phone 56. As discussed in detail herein, the system provides the user's temperature and alerts via a mobile application. Similarly, the system 410 could be embedded and implemented within the digital display 413 of a wristwatch 415, as illustrated in FIG. 16B. As shown in FIG. 16C, the system 410 may be embedded in the touchscreen display 413 of a tablet or laptop computer 417. Exemplary embodiments integrate or embed the system for measuring vital signs in cases for commonly used devices. FIG. 17 shows the system 410 embedded within a mobile phone case 419. These embodiments may include a battery powering the system which may be charged wirelessly or via a mini USB port.

In operation, the user affixes the vital signs monitoring device 10 to his or her mobile phone 56 by pressing the sticky surface on the back side 16 of the housing 12 onto the phone. Alternatively, the user puts a wearable vital signs monitoring device 110, 210 on herself by sliding a bracelet 110 onto her wrist, enclosing the wristband 211 of device 210 on her wrist, putting a necklace device around her neck, or slipping a ring device onto her finger. The user can download the mobile application 52 to interface and setup the system. To measure his vital signs 54, the user presses and holds the button 18. For the wearables such as the ring, bracelet, necklace, watch, etc., the user presses a measurement button. For measuring vital signs with devices embedded in or integrated within the digital touchscreen display or monitor of cell phones, tablets, PDMs, laptops, LCD monitors, watches, the user touches the display. Once touched, pressed, or clicked, it stays on for a pre-determined period of time, e.g., five minutes, and then automatically shuts off.

As the user touches or presses and holds the button 18, the system measures the user's temperature, heart rate, and/or blood pressure. More particularly, when the user pushes the ON/MEASURE button 18, the vital signs data is measured by the device 10, 10, a, 110, 210, 310, analyzed by the onboard computerized circuitry 20 to calculate and determine the human vital signs information 54, and transmitted to the mobile phone or other personal computing device 56 via Bluetooth to present it on the mobile app 52. After a few seconds of button holding, the results will be transmitted to the cellular phone 56 via Bluetooth 45 and displayed on the mobile application 52. Transmission via Bluetooth technology utilizes BT radio circuitry 30 to pair with a cellular phone 56 and transfer the data to the mobile app 52.

If the device is to be used as a stand-alone 310 without the mobile app, it will give the reading on small screen embedded into it and may include a memory chip to store data. As discussed, above, the user can receive alerts 46 in the event of vitals abnormalities like high temperature and high heart rate/blood pressure. These alerts 46 could be in the form of visual feedback by different colored LEDs 48, 50. The system detects and alerts the user about her vitals abnormalities via the mobile app 52, and the alerts may be audible and/or visual. In exemplary embodiments, the vital signs monitoring device 10 obtains human body temperature data using thermal sensors (Thermistors, heat resistors, microchip heat sensors, etc.). The device 10, 10a, 110, 210, 310 does the measurement by sensing the finger temperature by the sensor and calculates the exact body temperature using an electronic system (minicomputer).

As discussed above, the user can receive proximity alerts showing a "Safety Circle" within which the user can stay to maintain a safe distance from users with elevated temperatures. The user can define his or her proximity safe zone and "Safety Circle" perimeter via the mobile app or work with the system defaults. The user will receive audible and/or visual alerts warning him when he is getting close to a region with high temperature people, or "HOT ZONE". By observing these alerts, users can avoid HOT ZONES, which contain many potentially ill people. For example, the mobile app identifies symptomatic individuals, detecting potential infected symptoms and alerting users to avoid these individuals to avoid virus spread. As a "HOT PERSON" is approaching the user will be notified to ensure safe social distance to avoid infection. The system also categorizes a user's symptoms and reports/shares the information with a global database to be shared with media, authorities, and health organizations, assisting with combating viruses and raising social distance awareness. In exemplary embodiments, the system analyzes users' vital signs reports and recommends them to self-quarantine in case of suspicious symptoms.

Thus, it is seen that devices, systems, and methods for measuring vital signs are provided which allow emergency location and tracking ability. It should be understood that any of the foregoing configurations and specialized components or connections may be interchangeably used with any of the systems of the preceding embodiments. Although illustrative embodiments are described hereinabove, it will be evident to one skilled in the art that various changes and modifications may be made therein without departing from the scope of the disclosure. It is intended in the appended claims to cover all such changes and modifications that fall within the true spirit and scope of the present disclosure.

What is claimed is:

1. A device for measuring vital signs, comprising:
   a housing having a front side and a back side, the front side having a pressable button;
   an electronic circuit within the housing, the electronic circuit measuring and recording vital signs data when activated;
   an artificial intelligence unit within the housing, the artificial intelligence unit storing, recording, and analyzing the vital signs data;
   a geolocation system; and
   a hot zones database and a body temperature map containing information about regions with people reporting elevated body temperature;
   wherein the vital signs data comprise one or more of: body temperature, heart rate, blood pressure, and blood oxygenation level.

2. The device of claim 1 wherein the device provides proximity alerts to users showing a Safety Circle so users can maintain distance from users with elevated temperatures.

3. The device of claim 1 further comprising a control logic configured to monitor and update the vital signs data and a user's location.

4. The device of claim 1 wherein the enclosure is one of: a bracelet, a neckless, or a ring.

5. The device of claim 1 wherein the housing is in the shape of a round or pill-shaped button.

6. The device of claim 1 wherein the pressable button is located in the center of the front side of the housing.

7. The device of claim 1 further comprising an optical system that obtains vital signs data from a finger of a user.

8. The device of claim 1 further comprising an artificial intelligence unit.

9. The device of claim 1 wherein the electronic circuit is activated by pressing or touching and holding the pressable button.

10. The device of claim 1 further comprising a button battery within the housing.

11. The device of claim 1 further comprising a temperature-sensing microchip for body temperature measurement within the housing.

12. The device of claim 1 further comprising wireless capability to communicate the vital signs data to an external device.

13. The device of claim 1 wherein the electronic circuit works in conjunction with a web-based application and a mobile application for a mobile device.

14. The device of claim 1 wherein the entire front side consists of the pressable button.

15. The device of claim 1 wherein one half of the front side has a circular portion with a pressable button in the center of the circular portion.

* * * * *